(12) United States Patent
Yamane et al.

(10) Patent No.: US 8,944,994 B2
(45) Date of Patent: Feb. 3, 2015

(54) DEVICE FOR STERILIZATION CHECK (75) Inventors: Kenji Yamane, Kanagawa (JP); Shozo Iyama, Kanagawa (JP); Yasuyuki Hosono, Kanagawa (JP); Yasunori Ohta, Kanagawa (JP); Takao Ozaki, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 44 days.

(21) Appl. No.: 13/550,523

(22) Filed: Jul. 16, 2012

(65) Prior Publication Data
US 2013/0053635 A1    Feb. 28, 2013

(30) Foreign Application Priority Data

Aug. 22, 2011    (JP) .................................. 2011-180566

(51) Int. Cl.
*A61B 1/00*    (2006.01)
*A61L 2/28*    (2006.01)
*A61B 1/012*    (2006.01)

(52) U.S. Cl.
CPC . *A61L 2/28* (2013.01); *A61B 1/012* (2013.01); *A61L 2202/24* (2013.01)
USPC .......................................... 600/104; 600/153

(58) Field of Classification Search
CPC ........ A61L 2/28; G01N 31/226; A61B 1/012; A61B 1/121; A61B 2019/346
USPC .................................................. 600/133, 155
See application file for complete search history.

(56) References Cited

U.S. PATENT DOCUMENTS 6,010,662 A * 1/2000 Lin et al. ......................... 422/33

FOREIGN PATENT DOCUMENTS

JP    2002-355297 A    12/2002
JP    2005-204826 A    8/2005

* cited by examiner

*Primary Examiner* — Anhtuan T Nguyen
*Assistant Examiner* — Alexandra Newton
(74) *Attorney, Agent, or Firm* — McGinn IP Law Group, PLLC (57) ABSTRACT A device for sterilization check for an endoscope, comprising:
an elongated insertion member insertable into an inner pipeline of the endoscope, wherein
a plurality of indicator holding members each capable of holding a sterilization indicator for checking a sterilization effect by a sterilizing medium introduced to the inner pipeline are arranged on the insertion member along a longitudinal direction of the insertion member, and
ones of the indicator holding members adjacent to each other along the longitudinal direction of the insertion member are coupled together via a flexible coupling member deformable along a shape of the inner pipeline of the endoscope.

20 Claims, 8 Drawing Sheets

DEVICE FOR STERILIZATION CHECK

BACKGROUND OF THE INVENTION

1. Field of the Invention

The present invention relates to a device for sterilization check and, in particular, to a device for sterilization check capable of checking a sterilization effect on an internal pipeline of an endoscope.

2. Description of the Related Art

Medical endoscopes perform an observation of organs and the like by having an insertion unit inserted into a body cavity, or various remedies and treatments by using a treatment instrument inserted into a treatment instrument insertion path (which is also referred to as a "treatment tool insertion channel or a "forceps channel") of the endoscope. Therefore, when an endoscope having once been used is to be reused for another patient, the endoscope is required to be disinfected and sterilized after the end of examination and treatment to prevent infection between patients via the endoscope. Disinfection or sterilization is achieved by methods of using a disinfectant liquid, ethylene oxide gas, formalin gas, hydrogen peroxide gas plasma, ozone, a sterilized autoclave which uses water vapor high temperature and high pressure, and others.

A hydrogen peroxide plasma method is a typical advanced sterilizing methodology for endoscopes. In this method, hydrogen peroxide is decomposed with plasma to generate active hydroxy radicals, thereby achieving sterilization. Also, using an autoclave that sterilizes an endoscope with steam at high temperature and high pressure is a disinfecting and sterilizing methodology that has been widespread. Either methodology has many advantages, such as a highly reliable sterilization effect, free of residual toxicity, and low running cost.

In this sterilizing process, an operation of checking whether the sterilization effect by that sterilizing process has been sufficiently obtained is normally performed. In this checking operation, a sterilization indicator indicating that a subject to be sterilized has been subjected to the sterilizing process is used. The sterilization indicator indicates that the subject to be sterilized has been exposed to a sterilizing medium (heat or gas) for a predetermined period of time, and is a member having a non-reversible discoloration characteristic. In general, the sterilization indicator having this discoloration characteristic is a card-shaped, label-shaped, or tape-shaped material, and may be directly affixed to a medical instrument such as an endoscope or may be enclosed in a hermetically-sealed package. A doctor or a nurse checks the color of the sterilization indicator when opening the hermetically-sealed package and, if the color is changed to a predetermined color, believes that the sterilizing process is complete and uses the instrument for examinations, operations, and others.

In the case of a medical instrument configured not to have an elongated pipeline in the subject to be sterilized, a general sterilization indicator is affixed to the surface of the subject to be sterilized, thereby allowing the sterilization effect to be checked.

However, the inner pipeline of the endoscope has an elongated pipeline structure, which is difficult to check whether the sterilizing medium has reliably reached the inside of the inner pipeline. Therefore, even if the surface of the endoscope is exposed to the sterilizing medium, it is not known whether this sterilizing medium has passed through the inner pipeline, and the operation of checking whether the sterilizing process has been appropriately performed is not sufficient.

Japanese Patent Application Laid-Open No. 2002-355297 suggests an indicator for sterilization check, in which a linear subject having attached thereto a sterilization indicator composite is inserted in a narrow pipeline to allow sterilization in the pipeline to be checked.

Japanese Patent Application Laid-Open No. 2005-204826 suggests, as a device for sterilization check suitable for checking a sterilization effect on an elongated inner pipeline as an endoscope, a device including a pipeline tube having a variable pipeline diameter and an indicator case connected to the pipeline tube and capable of accommodating an indicator for sterilization check in a space communicating with an inner space of the pipeline tube.

SUMMARY OF THE INVENTION

Meanwhile, in the indicator for sterilization check described in Japanese Patent Application Laid-Open No. 2002-355297, in order to facilitate insertion into a simple pipeline such as a catheter, the linear subject having attached thereto the sterilization indicator composite is entirely covered with resin to ensure its stiffness.

Figure 7:
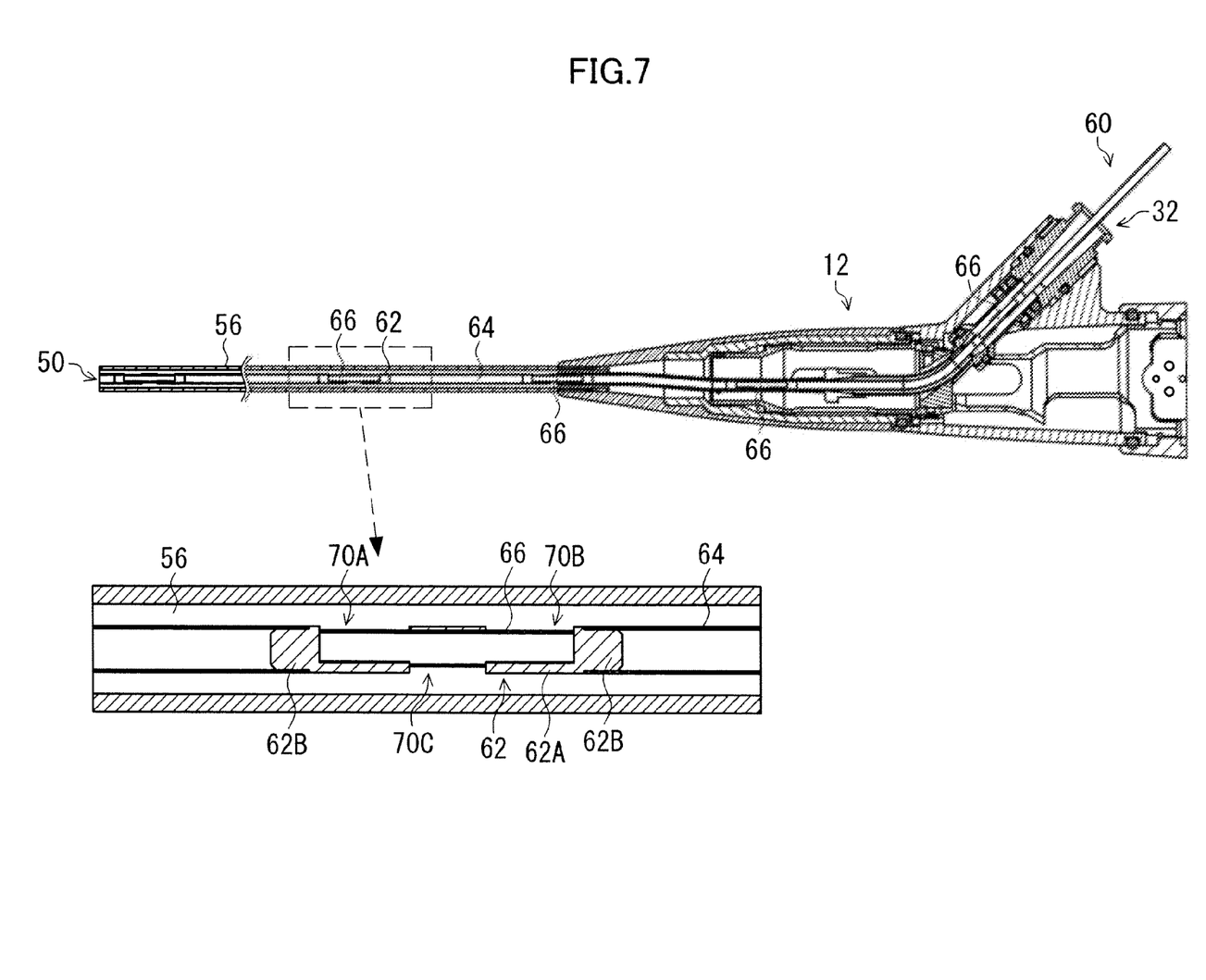
FIG. 7 is a sectional view showing the state in which the device for sterilization check is inserted into a treatment instrument insertion path of the endoscope.

However, the inner pipeline of the endoscope is elongated, for example, as a treatment instrument insertion path 56 shown in FIG. 7, and is also a bent pipeline. Therefore, if a portion with a high stiffness successively continues over its entire longitudinal direction, as the indicator for sterilization check described above, it is difficult to let the bent part of the inner pipeline of the endoscope pass through, and the indicator for the sterilization check described above cannot be inserted into the inner pipeline of the endoscope.

In the device for sterilization check described in Japanese Patent Application Laid-Open No. 2005-204826, a pipeline corresponding to the inner pipeline of the endoscope is configured by simulation, and based on a change of the indicator for sterilization check accommodated in the space communicating with the inner space of the pipeline the sterilization effect on the inner pipeline of the endoscope is checked. That is, in this device for sterilization check, the sterilization effect is indirectly checked by using the pipeline obtained by simulating the inner pipeline of the endoscope, and the sterilization effect on the inner pipeline of the endoscope cannot be directly checked. Moreover, the number of places to be measured is one, and it is merely confirmed that the sterilizing medium has passed through the inside of the pipeline configured by simulation. This is not sufficient as a check of the sterilization effect.

The present invention was made in view of these circumstances, and has an object of providing a device for sterilization check capable of reliably checking a sterilization effect on an inner pipeline of an endoscope even in a place that is difficult to reach by a sterilizing medium.

To achieve the object described above, a device for sterilization check for an endoscope according to the present invention comprising an elongated insertion member insertable into an inner pipeline of the endoscope, wherein a plurality of indicator holding members each capable of holding a sterilization indicator for checking a sterilization effect by a sterilizing medium introduced to the inner pipeline are arranged on the insertion member along a longitudinal direction of the insertion member, and ones of the indicator holding members adjacent to each other along the longitudinal direction of the insertion member are coupled together via a flexible coupling member deformable along a shape of the inner pipeline of the endoscope.

According to the present invention, the plurality of sterilization indicators are arranged over the entire inner pipeline of the endoscope. Therefore, the sterilization effect on the inner pipeline of the endoscope can be reliably checked even in a place that is difficult to reach by a sterilizing medium.

DETAILED DESCRIPTION OF THE PREFERRED EMBODIMENTS

A preferred embodiment of the present invention is described in detail below according to the attached drawings.

First, the structure of an endoscope to which a device for sterilization check of the present embodiment is applied is described.

Figure 1:
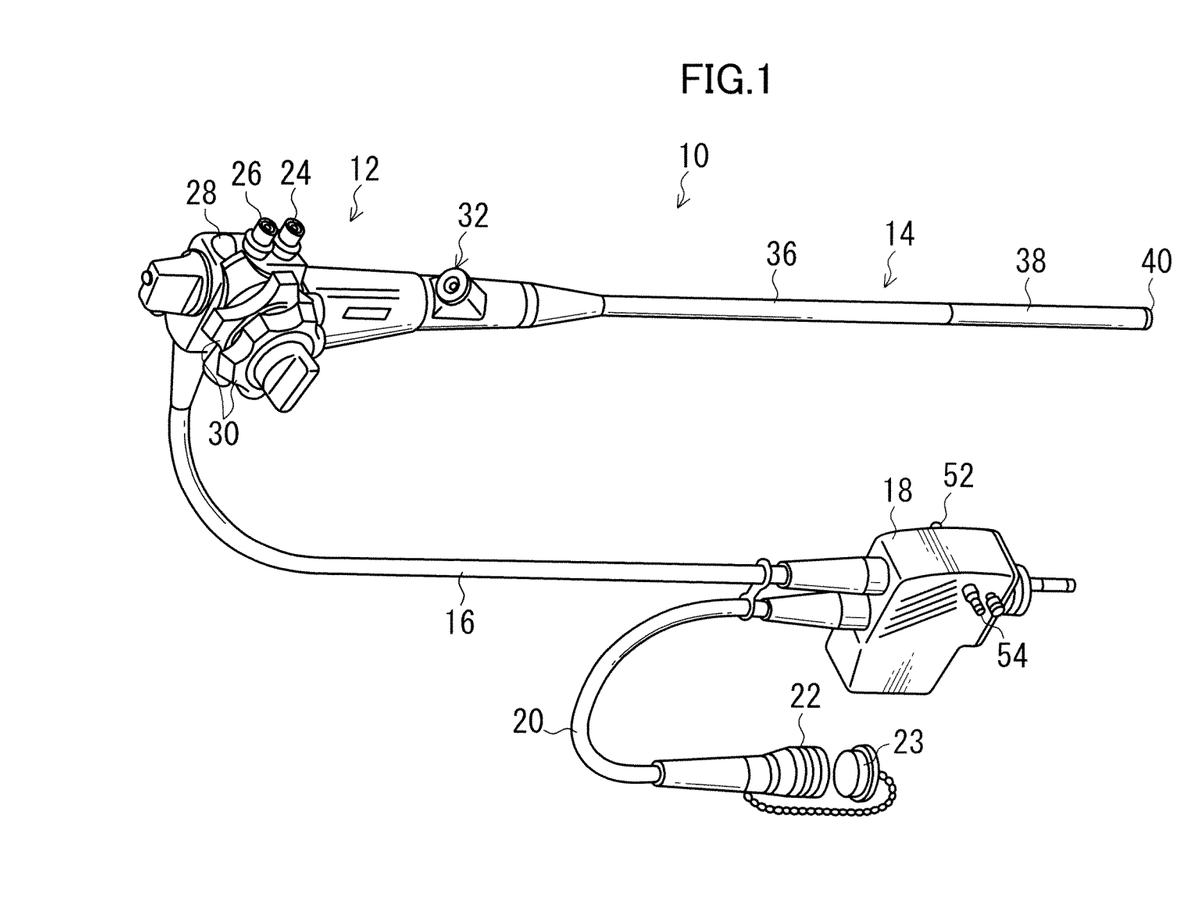
FIG. 1 is an external view showing an entire structure of an endoscope.

FIG. 1 is an external view showing an entire structure of the endoscope. As shown in this drawing, an endoscope 10 includes a handy operating part 12 and an insertion part 14 to be connected to this handy operating part 12 and inserted into a body cavity.

A universal cable 16 is connected to the handy operating part 12, and a light guide (LG) connector 18 is provided at the tip of this universal cable 16. The LG connector 18 is removably coupled to a light source device not shown, thereby causing illumination light to be sent to an illumination window 46 (refer to FIG. 2), which will be described further below. Also, an electrical connector 22 is connected to the LG connector 18 via a cable 20, and the electrical connector 22 is removably coupled to a processor not shown. Note that a reference numeral 23 of FIG. 1 denotes a cap of the electrical connector 22, and is mounted on the electrical connector 22 at the time of cleaning and disinfection.

The handy operating part 12 is provided with an air-supply/water-supply button 24, a suction button 26, and a shutter button 28 side by side with each other, and is provided also with paired angle knobs 30. Furthermore, the handy operating part 12 is provided with a treatment instrument insertion opening 32 into which a treatment instrument such as forceps is inserted.

The insertion part 14 is configured of a soft part (a flexible pipe part) 36, a bending part 38, undo tip part 40, sequentially from a handy operating part 12 side.

The bending part 38 is remotely operated to be bent by rotating the angle knobs 30 of the handy operating part 12. With this, the tip part 40 can be oriented to a desired direction.

Figure 2:
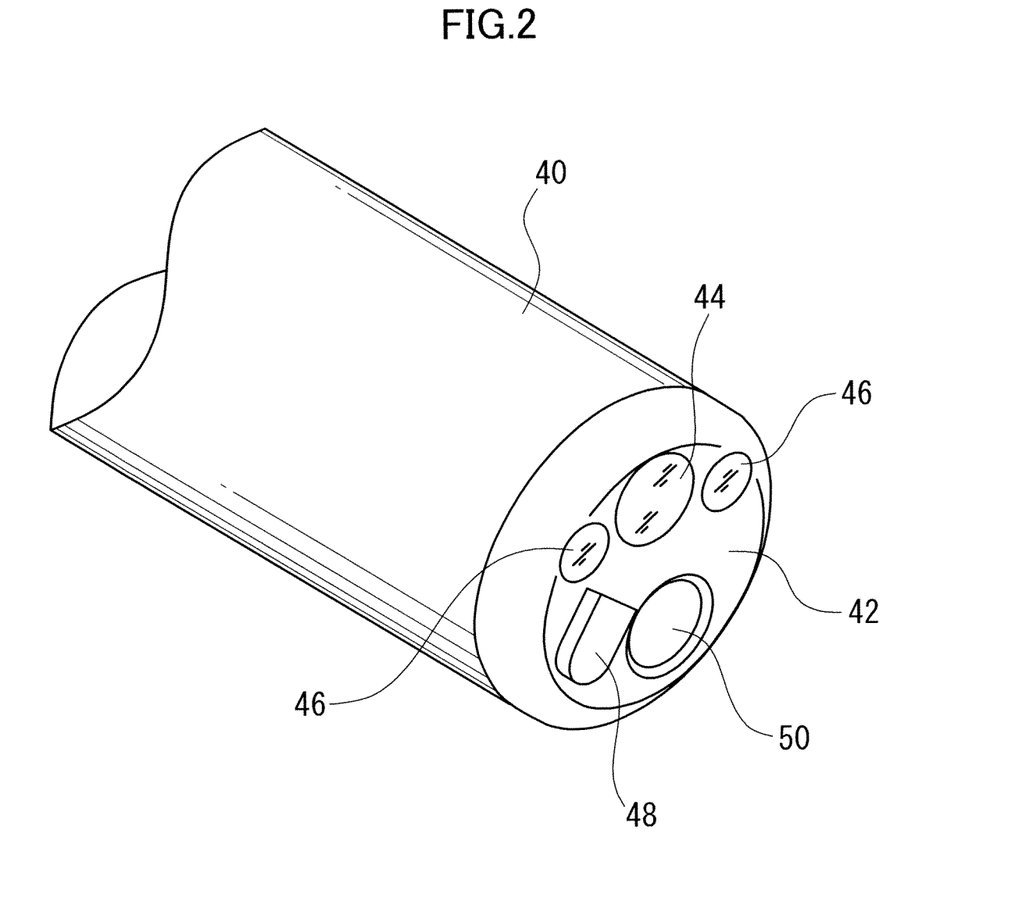
FIG. 2 is a perspective view showing a tip part of an insertion part of the endoscope shown in FIG. 1.

As shown in FIG. 2, the tip part 40 has an end surface 42 provided with an observation window 44, illumination windows 46, an air-supply/water-supply nozzle 48, and a forceps opening 50.

Behind the observation window 44, a CCD (not shown) is disposed, and a signal cable (not shown) is connected to a substrate supporting this CCD. The signal cable is inserted into the insertion part 14, the handy operating part 12, the universal cable 16, the LG connector 18, and the cable 20 of FIG. 1 to extend to the electrical connector 22, and is connected to processor not shown. Thus, an observed image captured at the observation window 44 is formed on a light-receiving surface of the CCD and is converted to an electrical signal, and this electrical signal is outputted via the signal cable to the processor to be converted to a video signal. With this, an observation image is displayed on a monitor (not shown) connected to the processor.

Behind the illumination windows 46 of FIG. 2, an outgoing end of a light guide (not shown) is disposed. This light guide is inserted into the insertion part 14, the handy operating part 12, and the universal cable 16 of FIG. 1, and has its incoming end disposed in the LG connector 18. Therefore, with the LG connector 18 being coupled to the light source device (not shown), illumination light emitted from the light source device is transmitted via the light guide to the illumination windows 46, and is applied from the illumination windows 46 onto an observation range ahead.

The air-supply/water-supply nozzle 48 communicates with an air-supply/water-supply valve (not shown) operated by the air-supply/water-supply button 24 of FIG. 1 via an air-supply/water-supply pipeline (not shown). Furthermore, this air-supply/water-supply valve communicates with an air-supply/water-supply connector 52 provided on the LG connector 18. To the air-supply/water-supply connector 52, air-supply/water-supply means not shown is connected and, from this air-supply/water-supply means, air and water are supplied. Therefore, by operating the air-supply/water-supply button 24, air or water is injected from the air-supply/water-supply nozzle 48 toward the observation window 44.

The forceps opening 50 communicates with a treatment instrument insertion opening 32 via a treatment instrument insertion path (not shown in FIG. 1 and is denoted as 56 in FIG. 7). Thus, with a treatment instrument such as forceps being inserted from the treatment instrument insertion opening 32, this treatment instrument can be led from the forceps opening 50. The forceps opening 50 also communicates with a suction valve (not shown) operated by the suction button 26 of FIG. 1, and this suction valve is further connected to a suction connector 54 of the LG connector 18. Therefore, with suction means not shown being connected to the suction connector 54 and the suction valve being operated with the suction button 26, a lesion area can be suctioned from the forceps opening 50.

Next, the device for sterilization check of the present embodiment is described.

Figure 3:
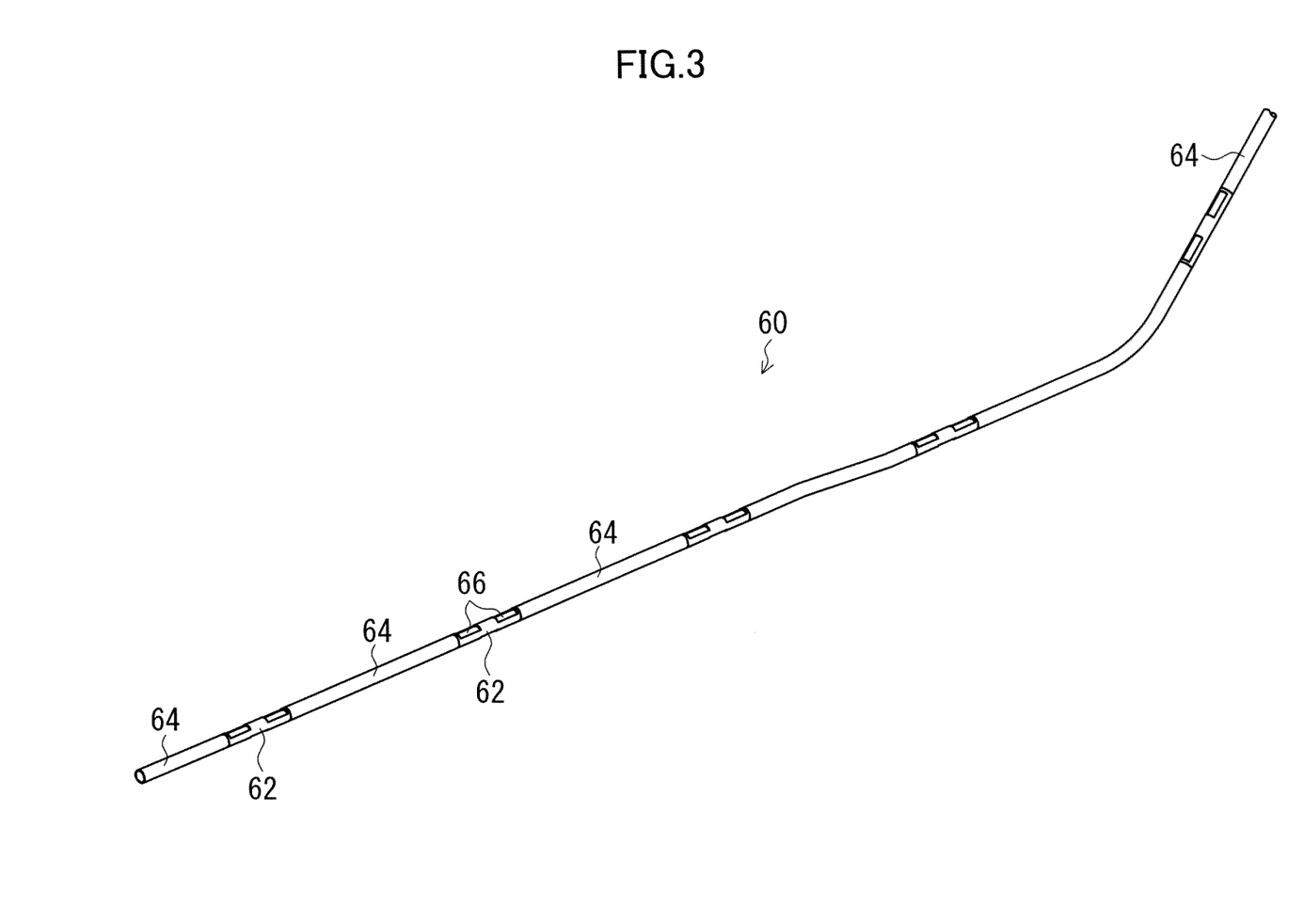
FIG. 3 is an external perspective view showing a device for sterilization check.
Figure 4:
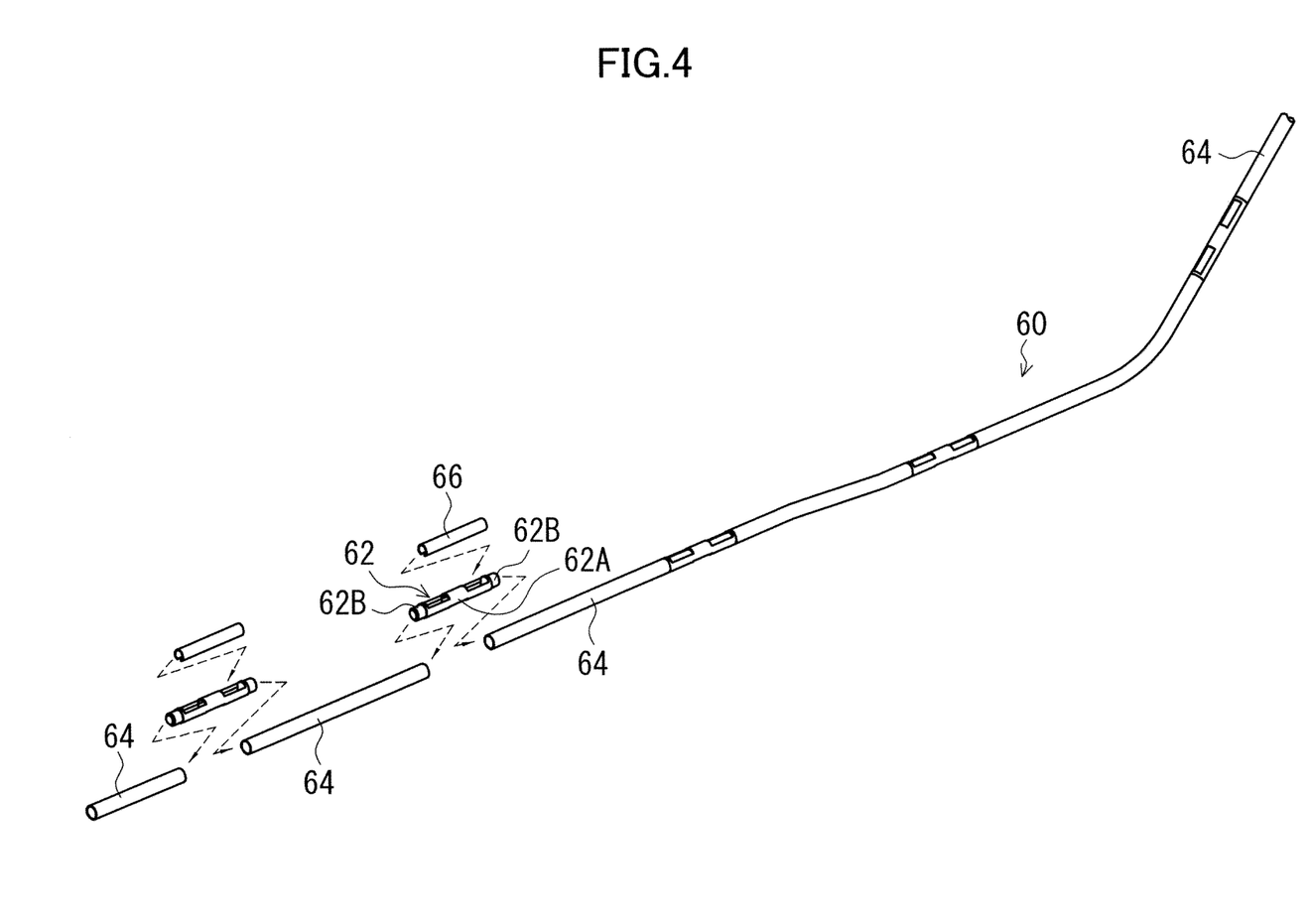
FIG. 4 is an exploded perspective view showing part of the device for sterilization check as being exploded.
Figure 5A:
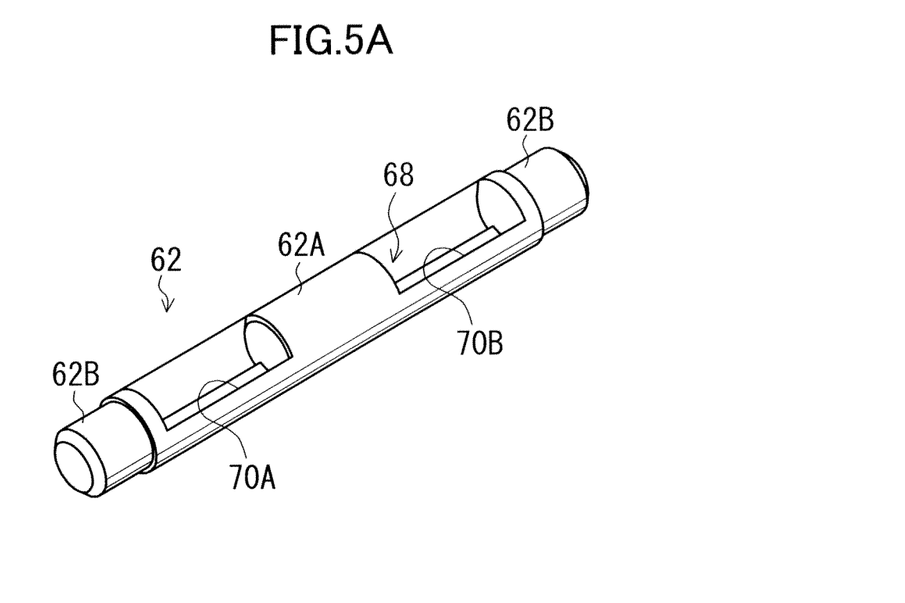
FIGS. 5A and 5B are external perspective views showing an indicator holder.
Figure 5B:
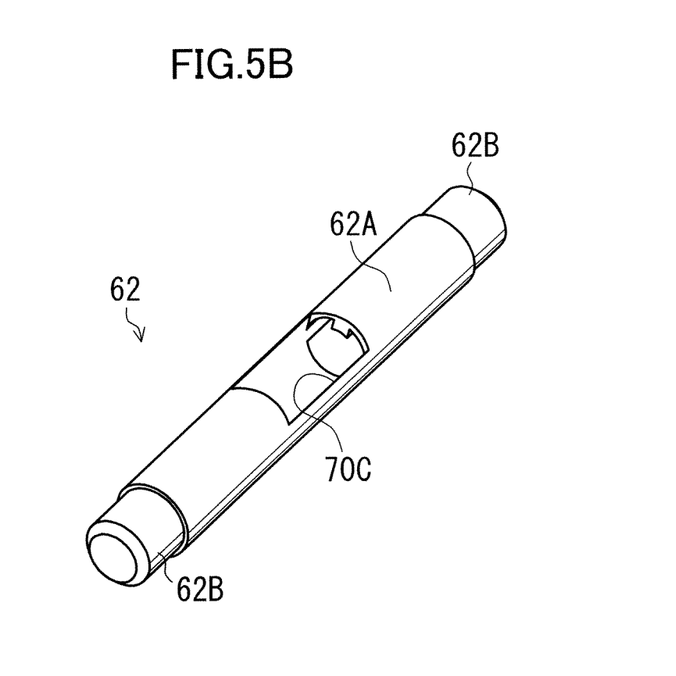

FIG. 3 is an external perspective view showing the device for sterilization check of the present embodiment. FIG. 4 is an exploded perspective view showing part of the device for sterilization check. FIGS. 5A and 5B are external perspective views showing an indicator holder, which is a component of the device for sterilization check of the present embodiment. Note that FIG. 5A is a drawing that shows the state of the indicator holder when viewed from a front surface side, and FIG. 5B is a drawing that shows the state of the indicator holder when viewed from a back surface side.

As shown in FIG. 3, FIG. 4, FIG. 5A, and FIG. 5B, a device for sterilization check 60 of the present embodiment is formed of an elongated insertion member insertable into a treatment instrument insertion path (not shown in FIG. 1 and is denoted as 56 in FIG. 7) provided inside the insertion part 14 of the endoscope 10 shown in FIG. 1. On this insertion member along its longitudinal direction, a plurality of indicator holders 62 are arranged a predetermined space apart from each other, and these indicator holders 62 are coupled to each other with tube bodies 64. Note that the insertion member has both ends each configured also of the tube body 64.

The indicator holder 62 is a holding member for holding a sterilization indicator 66. As shown in FIG. 4, FIG. 5A, or FIG. 5B, this indicator holder 62 is configured of a cylindrical body part 62A having an outer diameter approximately equal to the outer diameter of the tube body 64 and coupling parts 62B arranged at both ends of the body part 62A and each having an outer diameter smaller than the outer diameter of the body part 62A and approximately equal to the inner diameter of the tube body 64.

In the body part 62A of the indicator holder 62, an indicator accommodating part (a recessed part) 68 capable of replaceably accommodating the sterilization indicator 66 is provided. On a side surface of the body part 62A, a plurality of openings (window parts) 70A, 70B, and 70C are formed for exposing the sterilization indicator 66 accommodated in the indicator accommodating part 68 to the front surface.

The first and second openings 70A and 70B are arranged on an outer circumferential surface of the body part 62A at the positions same in a circumferential direction but different in an axial direction (both of end positions in the axial direction). The third opening 70C is arranged on the outer circumferential surface of the indicator holder 62 at a position opposite to the first and second openings 70A and 70B in the circumferential direction and at an approximately center part in the axial direction. The outer circumferential surface (an outer wall part) of the body part 62A except these openings 70A, 70B, and 70C functions as a support part (a dropping-off preventive member) preventing the sterilization indicator 66 accommodated in the indicator accommodating part 68 from dropping off.

The coupling parts 62B of the indicator holder 62 are each a portion fitting in an end opening of the tube body 64 to be coupled to the tube body 64. Although not shown, preferably, as members for preventing the coupling the indicator holder 62 and the tube body 64 from being easily released (a coupling-release preventive member), a projection is formed on either one surface of the inner circumferential surface of the tube body 64 and the outer circumferential surface of the coupling part 62B, and a recessed part that can be engaged with the projection is provided on the other surface. In this case, the coupling therebetween is not released unless a force equal to a predetermined value or more is applied in a direction in which the indicator holder 62 and the tube body 64 are away from each other.

The coupling between the indicator holder 62 and the tube body 64 is not meant to be restricted to the embodiment described above. For example, the indicator holder 62 and the tube body 64 may be coupled together by forming a male thread on the outer circumferential surface of the coupling part 62B and forming a female thread on the inner circumferential surface of the tube body 64 and screwing the indicator holder 62 and the tube body 64 with these threads. Also, in another embodiment, the indicator holder 62 and the tube body 64 may be coupled together via an adhesive.

The sterilization indicator 66 is to check the sterilization effect of the sterilizing means introduced to the inner pipeline (for example, a treatment instrument insertion path) of the endoscope 10, and a commercially-available chemical indicator (CI) or biological indicator (BI) is used. These indicators are well known, and are not described in detail herein.

The tube body 64 is a coupling member coupling adjacent indicator holders 62 together along the longitudinal direction of the device for sterilization check 60, is made of a soft resin having a stiffness lower than that of the indicator holder 62, and is configured to have flexibility allowing deformation along the shape of the inner pipeline of the endoscope 10. Note in the present embodiment that the coupling member coupling the indicator holders 62 together is not restricted to the tube body 64 but can be configured of a solid stick body.

Figure 6:
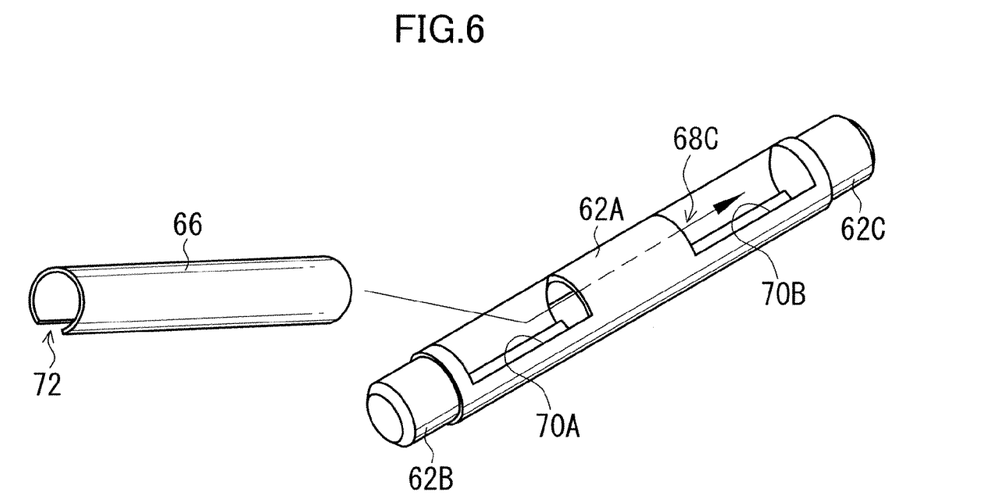
FIG. 6 is an explanatory diagram showing a method of accommodating an indicator.

FIG. 6 is an explanatory diagram showing a method of accommodating the sterilization indicator 66. The sterilization indicator 66 for use is formed by folding a sheet-like indicator sheet into a cylindrical shape. The sterilization indicator 66 is inserted and arranged from the opening 70A or 70B provided on the body part 62A of the indicator holder 62 into the indicator accommodating part 68. Here, since the sterilization indicator 66 is provided with a slit 72 along the axial direction, the sterilization indicator 66 can be inserted while the outer diameter of the sterilization indicator 66 is adjusted to an opening width of the opening 70A or 70B as an insertion opening of the indicator accommodating part 68. With this, insertion and arrangement into the indicator accommodating part 68 can be easily performed. When the sterilization indicator 66 is removed from the indicator accommodating part 68, a reversed procedure is performed.

Next, a method of checking the sterilization effect in the treatment instrument insertion path as an inner pipeline of the endoscope 10 by using the device for sterilization check 60 of the present embodiment is described. It is assumed herein that a process of cleaning the endoscope 10 has already been performed.

First, the device for sterilization check 60 is prepared. Here, if the sterilization indicator 66 is not accommodated in the indicator accommodating part 68 of each indicator holder 62, the sterilization indicator 66 is inserted and arranged into the indicator accommodating part 68 as shown in FIG. 6.

Next, as shown in FIG. 7, the device for sterilization check 60 is inserted from the treatment instrument insertion opening 32 provided on the handy operating part 12 of the endoscope 10 into the treatment instrument insertion path 56. Here, the inserting operation is performed until the tip part of the device for sterilization check 60 inserted in the treatment instrument insertion path 56 reaches the forceps opening 50 or is led to the outside from the forceps opening 50. With this, the plurality of sterilization indicators 66 are arranged over the entire area of the treatment instrument insertion path 56. Note that the device for sterilization check 60 is configured to be sufficiently longer than the length of the treatment instrument insertion path 56 in a longitudinal axis direction.

In this state, the endoscope 10 is set in a sterilizing device (for example, a hydrogen peroxide plasma sterilizing device). Then, the endoscope 10 is subjected to a sterilizing process in the sterilizing device for a predetermined period of time.

While the sterilizing process is being performed in the sterilizing device, the surface of the endoscope 10 is exposed to the sterilizing medium, the sterilizing medium (for example, hydrogen peroxide) enters from an open end of the treatment instrument insertion path 56, that is, the treatment instrument insertion opening 32 or the forceps opening 50, into the treatment instrument insertion path, and therefore the inside of the treatment instrument insertion path 56 is also exposed to the sterilizing medium. Here, since the device for sterilization check 60 is inserted and arranged in the treatment instrument insertion path 56, each sterilization indicator 66 of the device for sterilization check 60 reacts with the sterilizing medium with which the treatment instrument insertion path 56 is filled.

After the end of the sterilizing process, a sterilizing worker extracts the device for sterilization check 60 from the treatment instrument insertion path 56 of the endoscope 10 and checks the sterilization effect. Here, if the entire area of the treatment instrument insertion path 56 is filled with the sterilizing medium, each sterilization indicator of the device for sterilization check 60 appropriately react, and it can be confirmed that the sterilizing process in the treatment instrument insertion path 56 has been reliably performed. If all or part of the sterilizing indicators 66 does not appropriately reacts, the sterilizing medium may not have permeated the entire area of the treatment instrument insertion path 56 or the sterilizing device may have had some anomaly (trouble). In this case, some measures have to be taken, such as performing the sterilizing process again.

As has been described in the foregoing, according to the device for sterilization check 60 of the present embodiment, the plurality of indicator holders 62 are coupled to each other via the tube bodies 64. Therefore, the device for sterilization check 60 can be easily inserted in the inner pipeline (in this example, the treatment instrument insertion path 56 of FIG. 7) of the endoscope 10, and the plurality of sterilization indicators 66 can be arranged over the entire area of the inner pipeline. With this, the sterilization effect on the inner pipeline of the endoscope 10 can be reliably checked even in a place that is difficult for the sterilizing medium to reach.

Note that while the case has been exemplarily described in which the sterilization effect in the treatment instrument insertion path 56 as the inner pipeline of the endoscope 10 is checked in the present embodiment, this is not meant to be restrictive and the sterilization effect in another inner pipeline such as an air-supply/water-supply pipeline (an air-supply/water-supply channel), for example, can also be checked similarly.

Also, the device for sterilization check 60 may be of a disposable type (a throwaway type) or a reuse type (a repeatedly usable type). In the case of a reuse type, an operation of replacing the sterilization indicators 66 by new ones is required every time the device for sterilization check 60 is used. However, the components other than the sterilization indicators 66 can be used, and the reuse type is advantageous compared with the case of a disposable type in view of cost. By contrast, in the case of a disposable type, the device can be provided with the sterilization indicators 66 being accommodated in the indicator accommodating part 68 of each indicator holder 62 at the stage of manufacture and shipping. Therefore, the operation of replacing the sterilization indicators 66 is not required, and the work load on the sterilization worker can be reduced compared with the case of the reuse type.

Figure 8:
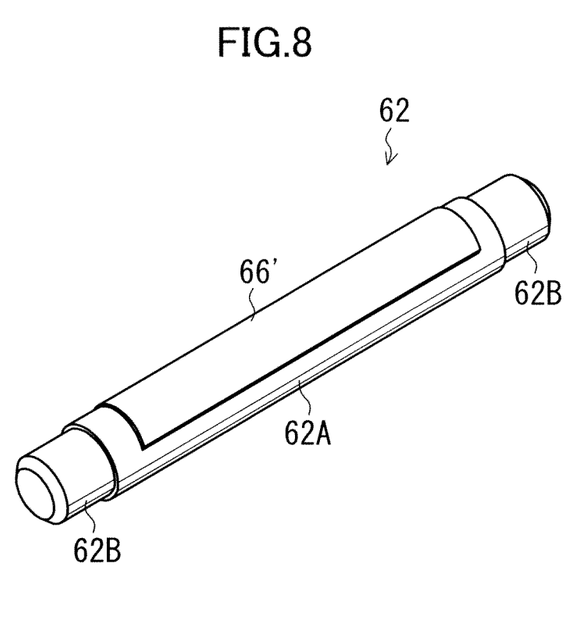
FIG. 8 is a perspective view showing another example of structure of the indicator holder.

Furthermore, while the indicator accommodating part (the recessed part) 68 for replaceably accommodating the sterilization indicators 66 is provided on the body part 62A of the indicator holder 62 in the present embodiment, this is not meant to be restrictive. For example, as shown in FIG. 8, a tape-shaped sterilizing indicator 66' may be affixed to the outer circumferential surface of the body part 62A of the indicator holder 62. In this case, the indicator accommodating part 68 (refer to FIG. 5A) is not required, and therefore the indicator holder 62 can be easily manufactured.

Still Further, the space between the indicator holders 62 for arrangement is not particularly restricted in the present embodiment, when the indicator holders 62 are equidistantly arranged, the sterilization effect on the inner pipeline of the endoscope 10 can be checked uniformly along the longitudinal direction of the inner pipeline.

On the other hand, the indicator holders 62 may be non-equidistantly arranged. For example, according to the shape of the inner pipeline of the endoscope or a distance from the end opening thereof, the space between the sterilization indicators for arrangement is made long in a place that is easy for the sterilizing medium to reach and, on the other hand, the space between the sterilization indicators for arrangement is made short in a place that is difficult for the sterilizing medium to reach. With this, the sterilization effect on the inner pipeline of the endoscope can be more efficiently checked.

Note that as a method of changing the space between the indicator holders 62 for arrangement, a plurality of tube bodies 64 having a plurality of lengths can be prepared, a tube body having a short length is used for connection when the space between the indicator holders 62 adjacent to each other is shortened, and a tube body having a long length is used for connection when the space is lengthened. With this, the space between the indicator holders 62 can be easily changed.

While the device for sterilization check of the present invention has been described in detail above, as a matter of course, the present invention is not meant to be restricted to the examples described above and may be variously improved or modified within a range not deviating from the gist of the present invention.

<Note>

As can be understood from the detailed description of the embodiment above, the specification includes disclosure of various technical ideas including the following aspects of the present invention.

(First Aspect):

A device for sterilization check for an endoscope, comprising: an elongated insertion member insertable into an inner pipeline of the endoscope, wherein a plurality of indicator holding members each capable of holding a sterilization indicator for checking a sterilization effect by a sterilizing medium introduced to the inner pipeline are arranged on the insertion member along a longitudinal direction of the insertion member, and ones of the indicator holding members adjacent to each other along the longitudinal direction of the insertion member are coupled together via a flexible coupling member deformable along a shape of the inner pipeline of the endoscope.

According to the first aspect of the present invention, the plurality of sterilization indicators are arranged over the entire inner pipeline of the endoscope, and therefore the sterilization effect on the inner pipeline of the endoscope can be reliably checked even in a place that is difficult to reach by a sterilizing medium.

(Second Aspect):

The device for sterilization check according to the first aspect of the present invention, wherein the coupling member is configured of a tube body.

According to the second aspect of the present invention, the device for sterilization check can be easily inserted even into an elongated bent inner pipeline.

(Third Aspect):

The device for sterilization check according to the first or second aspect of the present invention, wherein the indicator holding members are equidistantly arranged along the longitudinal direction of the insertion member.

According to the third aspect of the present invention, the sterilization indicators can be equidistantly arranged over the entire area of the inner pipeline of the endoscope, and therefore the sterilization effect on the inner pipeline of the endoscope can be uniformly checked along the longitudinal direction of the inner pipeline.

(Fourth Aspect):

The device for sterilization check according to the first or second aspect of the present invention, wherein the indicator holding members are non-equidistantly arranged along the longitudinal direction of the insertion member.

According to the fourth aspect of the present invention, according to the shape of the inner pipeline of the endoscope or a distance from the end opening thereof, a space between the sterilization indicators for arrangement can be made long in a place that is easy for the sterilizing medium to reach and, on the other hand, the space between the sterilization indicators for arrangement can be made short in a place that is difficult for the sterilizing medium to reach. With this, the sterilization effect on the inner pipeline of the endoscope can be more efficiently checked.

(Fifth Aspect):

The device for sterilization check according to the fourth aspect of the present invention, wherein ones of the indicator holding members adjacent to each other along the longitudinal direction of the insertion member have a space therebetween, the space being configured to be shorter as a distance from an end opening of the inner pipeline of the endoscope is longer.

According to the fifth aspect of the present invention, as the distance from the end opening of the inner pipeline of the endoscope is longer, the space between the sterilization indicators for arrangement is shorter, and therefore the sterilization effect can be more reliably checked even in a place that is difficult for the sterilizing medium to reach.

(Sixth Aspect):

The device for sterilization check according to any one of the first to fifth aspects of the present invention, wherein the indicator holding members are each provided with an indicator accommodation part capable of replaceably accommodating the sterilization indicator.

According to the sixth aspect of the present invention, the sterilization indictor is replaceably accommodated in the indicator holding members, and therefore the device for sterilization check can be reused.

(Seventh Aspect):

The device for sterilization check according to any one of the first to fifth aspects of the present invention, wherein the indicator holding members each have a surface to which the sterilization indicator is affixed.

According to the seventh aspect of the present invention, the structure of the indicator holding members can be simplified, and therefore can be easily manufactured.

(Eighth Aspect):

The device for sterilization check according to any one of the first to seventh aspects of the present invention, wherein the inner pipeline is a treatment instrument insertion path or an air-supply/water-supply path provided inside the endoscope.

According to the eighth aspect of the present invention, the sterilization effect on a treatment instrument insertion path or an air-supply/water-supply path of the endoscope can be reliably checked.

What is claimed is:

1. A device for sterilization check, comprising:
an endoscope having an insertion part for being inserted into a body cavity and an inner pipeline formed along a longitudinal axis direction of the insertion part; and
an elongated insertion member inserted into the inner pipeline of the endoscope,
wherein the insertion member comprises:
a sterilization indicator having reactivity to a sterilizing medium introduced to the inner pipeline;
a plurality of indicator holding members arranged along the longitudinal axis direction of the insertion member and each being capable of holding the sterilization indicator;
a coupling member which couples the indicator holding members adjacent to each other along the longitudinal direction of the insertion member and which is flexible and deformable along a shape of the inner pipeline of the endoscope; and
a plurality of openings formed on an outer circumferential surface of the insertion member for exposing the sterilization indicator.

2. The device for sterilization check according to claim 1, wherein the coupling member is configured of a tube body.

3. The device for sterilization check according to claim 1, wherein the indicator holding members are equidistantly arranged along the longitudinal direction of the insertion member.

4. The device for sterilization check according to claim 2, wherein the indicator holding members are equidistantly arranged along the longitudinal direction of the insertion member.

5. The device for sterilization check according to claim 1, wherein the indicator holding members are non-equidistantly arranged along the longitudinal axis direction of the insertion member.

6. The device for sterilization check according to claim 2, wherein the indicator holding members are non-equidistantly arranged along the longitudinal axis direction of the insertion member.

7. The device for sterilization check according to claim 5, wherein ones of the indicator holding members adjacent to each other along the longitudinal axis direction of the insertion member have a space therebetween, the space being configured to be shorter as a distance from an end opening of the inner pipeline of the endoscope is longer.

8. The device for sterilization check according to claim 6, wherein ones of the indicator holding members adjacent to each other along the longitudinal axis direction of the insertion member have a space therebetween, the space being configured to be shorter as a distance from an end opening of the inner pipeline of the endoscope is longer.

9. The device for sterilization check according to claim 1, wherein the indicator holding members are each provided with an indicator accommodation part capable of replaceably accommodating the sterilization indicator.

10. The device for sterilization check according to claim 2, wherein the indicator holding members are each provided with an indicator accommodation part capable of replaceably accommodating the sterilization indicator.

11. The device for sterilization check according to claim 1, wherein the indicator holding members each have a surface to which the sterilization indicator is affixed.

12. The device for sterilization check according to claim 2, wherein the indicator holding members each have a surface to which the sterilization indicator is affixed.

13. The device for sterilization check according to claim 1, wherein the inner pipeline comprises a treatment instrument insertion path or an air-supply/water-supply path provided inside the endoscope.

14. The device for sterilization check according to claim 2, wherein the inner pipeline comprises a treatment instrument insertion path or an air-supply/water-supply path provided inside the endoscope.

15. The device for sterilization check according to claim 9, wherein each opening of the plurality of openings corresponds to the indicator accommodation part.

16. The device for sterilization check according to claim 10, wherein each opening of the plurality of openings corresponds to the indicator accommodation part.

17. The device for sterilization check according to claim 9, wherein an outer wall part of the insertion member is configured as a dropping-off preventive member which prevents the sterilization indicator accommodated in the indicator accommodating part from dropping off.

18. The device for sterilization check according to claim 10, wherein an outer wall part of the insertion member is configured as a dropping-off preventive member which prevents the sterilization indicator accommodated in the indicator accommodating part from dropping off.

19. The device for sterilization check according to claim 1, wherein the coupling member comprises an adhesive.

20. The device for sterilization check according to claim 1, wherein the coupling member comprises a projection formed on an outer circumferential surface of the coupling member.

* * * * *